United States Patent [19]

König et al.

[11] 4,107,199
[45] Aug. 15, 1978

[54] BIS(ISOCYANATOPROPYL) ARYLACETONITRILES

[75] Inventors: Eberhard König, Leverkusen; Josef Pedain, Cologne, both of Germany

[73] Assignee: Bayer Aktiengesellschaft, Leverkusen, Germany

[21] Appl. No.: 763,219

[22] Filed: Jan. 27, 1977

[30] Foreign Application Priority Data

Feb. 7, 1976 [DE] Fed. Rep. of Germany ....... 2604831

[51] Int. Cl.² ............................................. C07C 121/66
[52] U.S. Cl. ........................ 260/465 D; 260/453 PH; 260/465 E; 528/44
[58] Field of Search ...... 260/465 D, 453 AR, 453 PH

[56] References Cited

U.S. PATENT DOCUMENTS

| 2,305,529 | 12/1942 | Hester et al. | 260/465 H |
| 2,865,940 | 12/1958 | Nobis et al. | 260/453 A |

Primary Examiner—Dolph H. Torrence
Attorney, Agent, or Firm—Gene Harsh; Joseph C. Gil; R. Brent Olson

[57] ABSTRACT

The instant invention relates to nitrilediisocyanates of the formula:

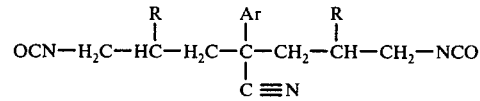

wherein
Ar represents an aromatic hydrocarbon group having 6 to 14 carbon atoms which may contain one or more substituents which are inert towards isocyanate groups and
R represents hydrogen or an aliphatic hydrocarbon group having 1 to 4 carbon atoms which may be used to prepare lightfast polyurethanes which readily adhere to various substances.

4 Claims, No Drawings

BIS(ISOCYANATOPROPYL) ARYLACETONITRILES

DESCRIPTION OF THE INVENTION

The instant invention relates to novel diisocyanates of the formula:

$$\text{OCN}-\text{H}_2\text{C}-\overset{\overset{R}{|}}{\text{HC}}-\text{H}_2\text{C}-\overset{\overset{Ar}{|}}{\underset{\underset{C\equiv N}{|}}{C}}-\text{CH}_2-\overset{\overset{R}{|}}{\text{CH}}-\text{CH}_2-\text{NCO}$$

in which
  Ar represents an aromatic hydrocarbon group having 6 to 14 carbon atoms which may contain one or more substituents which are inert towards isocyanate groups, and
  R represents hydrogen or an aliphatic hydrocarbon group having from 1 to 4 carbon atoms.

The invention also relates to a process for the preparation of these new diisocyanates, characterized in that a diamine of the formula $$\text{H}_2\text{N}-\text{CH}_2-\overset{\overset{R}{|}}{\text{CH}}-\text{CH}_2-\overset{\overset{Ar}{|}}{\underset{\underset{C\equiv N}{|}}{C}}-\text{CH}_2-\overset{\overset{R}{|}}{\text{CH}}-\text{CH}_2-\text{NH}_2$$

in which
  Ar and R have the meaning specified above, is phosgenated.

Finally, the invention relates to the use of the new diisocyanates as components for the production of polyurethanes by the isocyanate polyaddition process.

The novel diisocyanates with nitrile groups of the instant invention have numerous valuable properties:

1. The new diisocyanates have aliphatically bound isocyanate groups and are therefore suitable for the production of lightfast polyurethanes;
2. the new diisocyanates range from medium viscosity liquids to waxy solids with a low vapor pressure and are therefore more desirable from a physiological point of view than the known aliphatic diisocyanates (such as hexamethylene diisocyanate) which have a much higher vapor pressure;
3. the new diisocyanates have nitrile groups, with the result that polyurethanes produced from them adhere much more firmly to various substrates, wood, plastic surfaces such as PVC surfaces or glass. Moreover, polyurethanes produced from the new diisocyanates have improved oil resistance because of the presence of the nitrile groups.

The diisocyanates according to the invention are prepared from the corresponding diamines of the formula $$\text{H}_2\text{N}-\text{CH}_2-\overset{\overset{R}{|}}{\text{CH}}-\text{CH}_2-\overset{\overset{Ar}{|}}{\underset{\underset{C\equiv N}{|}}{C}}-\text{CH}_2-\overset{\overset{R}{|}}{\text{CH}}-\text{CH}_2-\text{NH}_2$$

by known processes, for example by the so-called cold-hot phosgenating process (W. Siefken, Annalen der Chemie, 562, (1949), pages 75 et seq) or by reaction with other suitable compounds, e.g. oxalyl chloride, to which inert organic solvents such as chlorobenzene may be added.

In the above formula and in the formula given below, Ar and R have the following meaning:

Ar represents an aromatic hydrocarbon group having from 6 to 14 carbon atoms which may contain one or more substituents which are inert towards isocyanate groups. These substituents may be, for example, halogen atoms, preferably chlorine, $C_1$-$C_4$ alkyl groups, preferably methyl groups, or $C_1$-$C_4$ alkoxy groups, preferably methoxy groups. Ar is preferably a phenyl, naphthyl, chlorophenyl, methoxyphenyl or methyl-phenyl group, most preferably a phenyl group.

R represents hydrogen or an aliphatic hydrocarbon group having from 1 to 4 carbon atoms, for example hydrogen, methyl, ethyl, propyl and butyl groups. It is preferably hydrogen or a methyl group, most preferably hydrogen.

The diamines of the above formula used for the process according to the invention may be prepared as follows:

As described by Bruson and Riener in J. Am. Chem. Soc. 64, 2850 (1942) or in U.S. Pat. No. 2,305,529, 2 mols of an acrylonitrile of the formula $$\text{CH}_2=\overset{\overset{R}{|}}{C}-\text{CN}$$

and 1 mol of an arylacetonitrile of the formula $$\text{Ar}-\text{CH}_2-\text{CN}$$

are first reacted together to produce a trinitrile of the formula $$\text{Ar}-\overset{\overset{\text{CH}_2-\text{CH(R)}-\text{CN}}{|}}{\underset{\underset{\text{CH}_2-\text{CH(R)}-\text{CN}}{|}}{C}}-\text{CN}$$

which is then hydrogenated as described below to the diamine used for the process according to the invention.

Suitable acrylonitriles include, for example, acrylonitrile itself, methacrylonitrile, ethyl acrylonitrile, propylacrylonitrile and butylacrylonitrile. Acrylonitrile and methacrylonitrile are preferred, and acrylonitrile is particularly preferred.

Suitable aryl-acetonitriles include, for example, phenylacetonitrile, naphthylacetonitrile, 4-chlorophenylacetonitrile, 4-methoxy-phenylacetonitrile and 4-methylphenyl-acetonitrile. Phenylacetonitrile is the presently preferred aryl-acetonitrile.

Conversion of the above mentioned trinitriles into the diamines with a nitrile group used in the process according to the invention may be carried out, for example, by catalytic hydrogenation in the presence of a weakly polar or non-polar organic solvent and ammonia. The reaction may be carried out at a temperature of 80° to 130° C and preferably a temperature of 100° to 120° C. It is also preferred to carry out the reaction under a pressure of from 120 to 200 bar, and in particular from 140 to 170 bar. It has been surprisingly found that under these conditions of hydrogenation, the trinitriles are selectively converted into the diamines used in the process according to the invention.

Suitable weakly polar or non-polar solvents include e.g. benzene, toluene, ethylbenzene, o-, m- or p-xylene, chlorobenzene and anisole. In addition to these aromatic solvents, aliphatic and cycloaliphatic hydrocarbons, such as octane, nonane, decane, cyclohexane or ethylcyclohexane, may also be used. Commercial solvent mixtures such as the usual commercial petroleum ethers may also be used, but it is preferred to use the above mentioned aromatic hydrocarbons. The solvent mixture may also contain up to a maximum of 20% by weight of polar solvent such as methanol, ethanol, propanol or benzyl alcohol, but the reaction is preferably carried out without the addition of the last mentioned polar solvents. The solvents used must, of course, be inert towards amino groups.

Suitable hydrogenation catalysts include e.g. Raney cobalt and Raney nickel, but other catalysts, such as those based on platinum or palladium, are also suitable.

When carrying out the hydrogenation reaction, it has been found advisable to suppress unwanted liberation of ammonia in known manner by using solvents admixed with ammonia.

The trinitriles used for hydrogenation are preferably dissolved as 15 to 40% by weight solutions in the above mentioned solvents or solvent mixtures.

The solutions of diamines obtained from the hydrogenation reaction may be freed from catalyst by filtration and then processed according to the invention without any further purification. If desired, the diamines can also be isolated in the pure form before they are phosgenated.

For carrying out the process according to the invention, the diamines are phosgenated in known manner, for example by the cold-hot phosgenating process mentioned above, and worked up by distillation. Phosgenation is preferably carried out in the presence of a suitable solvent such as chlorobenzene.

The diisocyanates according to the invention constitute a new type of aliphatic diisocyanates which are particularly characterized by the presence of a nitrile group. Because of this nitrile group, polyurethanes produced from the diisocyanates according to the invention have excellent adherence to various substrates. In addition, the polyurethanes are distinguished by their enhanced oil resistance.

When the diisocyanates according to the invention are used according to the invention, the usual procedures of polyurethane chemistry may be adopted. This means that the diisocyanates according to the invention, alone or in combination with generally known or used polyisocyanates of polyurethane chemistry, may be reacted with any active hydrogen containing compound, for example those described in "Kunststoff-Handbuch", Volume VII, Polyurethane, Carl-Hanser-Verlag, Munich (1966). The new diisocyanates are particularly suitable for the production of polyurethane adhesives and polyurethane lacquers.

The following Examples serve to explain the invention without restricting it.

Examples

Preparation of Starting Compounds

EXAMPLE 1

3-Phenyl-pentane-1,3,5-tricarboxylic acid trinitrile may be prepared by the method given by Bruson and Riener in J. Amer. Chem. Soc. 65, 23 (1943) or as described below:

450 g (8.5 mol) of acrylonitrile are added dropwise to a mixture of 468 g (4 mol) of benzyl cyanide, 14 g of potassium hydroxide (3%), 240 ml of dioxane and 160 ml of water at room temperature with stirring and at such a rate that the temperature is kept at 30 to 35° C, if necessary with cooling. Stirring is then continued for 2 hours to complete the reaction. The crystal paste is then acidified with dilute hydrochloric acid diluted with methanol/water, suction filtered and dried. 840 g (94% of the theory) of colorless crystals, m.p. 70° C, are obtained.

EXAMPLE 2

3-(4-Chloro-phenyl)-pentane-1,3,5-tricarboxylic acid trinitrile 212 g (4 mol) of acrylonitrile are added dropwise to a mixture of 302 g (2 mol) of 4-chloro-phenylacetonitrile, 10 g of potassium hydroxide, 400 ml of dioxane and 20 ml of water at 40° C with stirring and at such a rate that the temperature is kept at 40° to 45° C The reaction mixture is stirred for 6 hours at room temperature after all the acrylonitrile has been added. The crystalline paste obtained as precipitate is acidified with dilute hydrochloric acid, suction filtered, washed with methanol and dried. 450 g (87% of the theory) of colorless crystals, m.p. 122° C, are obtained.

EXAMPLE 3

4-Amino-1-aminopropyl-1-phenyl-butane-carboxylic acid nitrile 1800 g of the trinitrile compound prepared according to Example I are hydrogenated in 4500 ml of toluene in which 500 g of liquid ammonia are dissolved in a 10 liter autoclave in the presence of 200 g of Raney cobalt at 115° C and a pressure of 150 bar until no further hydrogen is taken up. After removal of the catalyst by filtration and concentration of the hydrogenated solution by evaporation under a vacuum of 14 Torr, a pale yellow oil is left behind. According to gas chromatographic determination, this oil contains the desired diamine in a degree of purity of 96%. The constitution of this diamine is confirmed by its IR, NMR and mass spectrum and by GC-MS coupling and quantitative analysis:

$C_{14}H_{21}N_3$ (231) Calculated: C 73.0 H 9.1 W 18.2 Found: 72.7 9.1 18.0

EXAMPLE 4

4-Amino-1-aminopropyl-1-phenyl-butane carboxylic acid nitrile (see Example 3)

600 g of the trinitrile compound prepared according to Example 1 are hydrogenated in a mixture of 1100 ml of cyclohexane, 100 ml of methanol and 250 g of liquid ammonia in a 3 liter autoclave in the presence of 70 g of Raney cobalt at 110° C and a pressure of 170 bar until uptake of hydrogen ceases. The hydrogenation product is then worked up as described in Example 3. The diamine is obtained in the form of a pale yellow oil which is 98% pure.

EXAMPLE 5

4-Amino-1-aminopropyl-1-(4-chlorophenyl)-butane carboxylic acid nitrile 500 g of the trinitrile compound prepared according to Example 2 are hydrogenated in 1400 ml of toluene and 200 g of ammonia in a 3 liter autoclave in the presence of 65 g of Raney cobalt at 115° C and a pressure of 150 bar until uptake of hydrogen ceases. After removal of the catalyst by filtration and concentration of the hydrogenated solution by evaporation under a vacuum of 14 Torr at 90° C, a pale yellow oil is left behind.

According to gas chromatographic determination, this oil contains the desired diamine in a degree of purity of 85%. $C_{14}H_{20}N_3Cl$ (265)

PROCESS ACCORDING TO THE INVENTION

EXAMPLE 6

4-Isocyanato-1-isocyanatopropyl-1-phenyl-butane carboxylic acid nitrile 3 liters of chlorobenzene, cooled to −15° C are saturated with 400 g of gaseous phosgene. To this phosgene solution, a solution of 462 g (2 mol) of the 96% diamine prepared according to Example 3 in 2 liters of chlorobenzene is added dropwise over a period of one hour with stirring. By the time all the diamine has been added, the reaction temperature has risen to about 2° C in spite of external cooling. The reaction mixture is then gradually heated to 70° C over a period of about 5 hours and at the same time a fine stream of phosgene is bubbled through the suspension with stirring. Then, while heating the reaction mixture under the same conditions, the temperature is raised to reflux (about 134° C) so that a clear, dark solution is obtained after about 16 hours. Nitrogen is blown through the solution and the solution is then freed from solvent by evaporation under a vacuum of 14 Torr. The residue is subjected to vacuum distillation. The main fraction boils at 200° to 205° C and 0.1 to 0.2 Torr. 435 g (about 81% of the theory) of a colorless oil is obtained, which after some time forms crystals melting at 38° C. The constitution of this diisocyanate is confirmed by the IR, NMR and mass spectrum and quantitative elementary analysis.

$C_{16}H_{17}N_3O_2$ (283)

Calculated: C 67.8 H 6.0 N 14.85

Found: 68.2 6.1 14.6

An Isocyanate content: (29.6% (corresponding to the theory) Hydrolyzable Cl content: 0.1%.

EXAMPLE 7

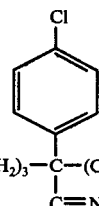
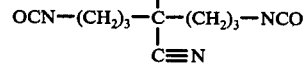

4-Isocyanato-1-isocyanatopropyl-1-(4-chlorophenyl)-butane carboxylic acid nitrile 490 g of the diamine prepared according to Example 5, which is 85% pure, is phosgenated and processed in the same way as described in Example 7. 260 g of an oil which boils at 230° to 240° C and 2 to 5 Torr and slowly solidifies on cooling is obtained.

The IR, NMR and mass spectrum confirm the constitution.

$C_{16}H_{16}N_3O_2Cl$ (317)

Isocyanate content: 25.5% (calculated: 26.4%).

What is claimed is:

1. Diisocyanates of the formula

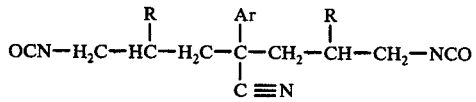

in which

Ar represents an aromatic hydrocarbon group having from 6 to 14 carbon atoms which may contain one or more substituents which are inert towards isocyanate groups and R represents hydrogen or an aliphatic hydrocarbon group having from 1 to 4 carbon atoms.

2. The diisocyanates of claim 1, wherein the substituents of the Ar group are selected from the group consisting of halogen atoms, $C_1$-$C_4$ alkyl groups, or $C_1$-$C_4$ alkoxy groups.

3. The diisocyanates of claim 1, wherein Ar represents a phenyl group.

4. The diisocyanates of claim 1, wherein R represents a hydrogen atom or methyl group.

* * * * *